United States Patent [19]

Mettes

[11] Patent Number: 5,589,085

[45] Date of Patent: Dec. 31, 1996

[54] PROCESS OF MANUFACTURING A DETECTING UNIT FOR AN ELECTROLYTIC CELL WITH THIN FILM ELECTRODES

[75] Inventor: Jacob Mettes, New Hope, Pa.

[73] Assignee: Meeco, Incorporated, Warrington, Pa.

[21] Appl. No.: 511,531

[22] Filed: Aug. 4, 1995

[51] Int. Cl.$^6$ .............................. C23F 1/02; G01N 27/26
[52] U.S. Cl. .................... 216/65; 73/335.02; 204/430; 205/788; 216/66; 216/75; 427/125
[58] Field of Search .................... 204/430; 205/788; 216/65, 66, 74, 75; 427/58, 123, 125; 73/335.02, 335.03, 335.04, 335.05

[56] References Cited

U.S. PATENT DOCUMENTS

| | | | |
|---|---|---|---|
| 2,993,853 | 7/1961 | Berry | 204/430 |
| 3,050,371 | 8/1962 | Dowson et al. | |
| 3,223,609 | 12/1965 | Reeds, Jr. | |
| 3,234,117 | 2/1966 | Rost et al. | |
| 3,614,855 | 10/1971 | Van Luik, Jr. | |
| 3,696,007 | 10/1972 | Bennett et al. | |
| 4,098,650 | 7/1978 | Sayles | |
| 4,216,669 | 8/1980 | Harding, Jr. | |
| 4,222,261 | 9/1980 | Leblanc et al. | |
| 4,356,834 | 11/1982 | LeMay | |
| 4,419,888 | 12/1983 | Kitamura et al. | |
| 4,490,211 | 12/1984 | Chen et al. | 216/65 |
| 4,535,620 | 8/1985 | Cunningham | |
| 4,568,632 | 2/1986 | Blum et al. | 216/65 |
| 4,589,971 | 5/1986 | Mayeaux | |
| 4,625,543 | 12/1986 | Ertl et al. | |
| 4,773,275 | 9/1988 | Kalinoski | |
| 4,800,000 | 1/1989 | Zatko et al. | |
| 4,842,709 | 6/1989 | Mayeaux | |
| 4,954,238 | 9/1990 | Kato et al. | 204/430 |
| 4,975,145 | 12/1990 | Yamazaki et al. | 216/65 |

FOREIGN PATENT DOCUMENTS

| | | |
|---|---|---|
| 3632698 | 3/1988 | Germany. |
| 485373 | 9/1975 | U.S.S.R. |

OTHER PUBLICATIONS

K. Sigiyama and T. Ohmi, "Ultraclean Gas Delivery Systems—Part I," *Microcontamination*, Nov. 1988, pp. 49–54.

T. Kimura, J. Mettes, and M. Schack, "Sub-ppb Analysis of Nitrogen Gas by APIMS," presented at Technical Symposium of Semicon East 89 in Boston, Massachusetts, Sep. 1989.

A. H. Miguel and D. F. S. Natusch, "Diffusion Cell for the Preparation of Dilute Vapor Concentrations," *Analytical Chemistry*, vol. 47, No. 9, pp. 1705–1707, Aug. 1975.

D. Smith and J. Mitchell, Jr., *Aquametry* (Part II), pp. 541, 663, 673–674, 790, 1128, 1151–1152, (2d ed. 1984) month or date unavailable.

(List continued on next page.)

*Primary Examiner*—T. Tung
*Attorney, Agent, or Firm*—Ratner & Prestia

[57] ABSTRACT

A new design for and an improved process of manufacturing a detecting unit for a type I electrolytic cell with thin film electrodes. In the first step of the process, a long, narrow, transparent, hollow glass tube is provided having an inside surface, an outside surface, and an end with a rim. A thin, noble metal film is deposited on the inside surface of the hollow glass tube. Then, a beam from a light source is directed through the hollow glass tube to remove a first portion of the noble metal film from the inside surface of the hollow glass tube and create a first spacer area. The beam also removes a second portion of the noble metal film from the inside surface of the hollow glass tube and creates a second spacer area. Consequently, two, separate electrode wires are created. Finally, an hygroscopic film is deposited on the entire inside surface of the hollow glass tube, covering completely the first and second electrode wires and the spacer areas. The detecting unit thus manufactured has a long, narrow, transparent, hollow glass tube; first and second thin, flat, noble metal, film electrodes deposited on the inside surface of the glass tube and separated by spacer areas; and an hygroscopic film deposited on the entire inside surface of the glass tube, covering completely the first and second electrodes and the spacer areas.

22 Claims, 6 Drawing Sheets

OTHER PUBLICATIONS

Paul D. Agnello and Thomas O. Sedgwick, "The Use of Gas Monitors to Characterize a Low–Temperature Atmospheric–Pressure Epitaxial System," *The Journal of the Electrochemical Society*, pp. 1–8 and 7 Figures month or date unavailable.

F. Mermoud, M. Brandt, and J. McAndrew, "Low–Level Moisture Generation," *Analytic Chemistry*, vol. 63, No. 3, pp. 198–202, 1991 month or date unavailable.

5,589,085

1

PROCESS OF MANUFACTURING A DETECTING UNIT FOR AN ELECTROLYTIC CELL WITH THIN FILM ELECTRODES

FIELD OF THE INVENTION

This invention relates to an electrolytic device for measuring water concentrations in gases. More particularly, the invention concerns an improved design for and process of manufacturing a specific component of an electrolytic device: the detecting unit of a type I electrolytic cell. The improved design and process provide for greater standardization, improved yields, superior detecting unit quality, and better cell performance in terms of a lower detection limit, a faster response time, and the elimination of undesirable recombination effects.

BACKGROUND OF THE INVENTION

In many industrial processes, the presence and amount of even minute moisture concentrations in flowing gas streams must be detected and measured with a high degree of speed and accuracy. The process of manufacturing semiconductors uses flowing gas streams, for example, and trace moisture concentrations present in those streams affect production yield. If moisture concentrations exceed specified limits, the contaminated gas stream may produce, at considerable expense, an unacceptable semiconductor lot. Thus, detection and measurement of moisture concentrations in industrial processes such as semiconductor production is required because moisture is often critical to the quality of the product made.

To meet the industrial demand, sensitive hygrometers are available which have extremely low detection limits and fast response times. The most sensitive and commercially available hygrometers can detect and measure moisture concentrations on the order of ten parts per billion by volume—although modern, high-purity hygrometers may reach limits of a few ppb. The prior art is replete with a variety of water detection and measurement devices, or hygrometers. These include infrared absorption-type hygrometers, conductivity cells, piezoelectric hygrometers, impedence-type type hygrometers, mirror dew point apparatuses, gas chromatographs (which may include an electron capture detector), and electrolytic hygrometers. A general discussion of such devices is found in U.S. Pat. No. 4,535,620, issued to R. Cunningham.

K. Sugiyama & T. Ohmi, "Ultraclean Gas Delivery Systems—Part I," in *Microcontamination* at 49–54 (November 1988), discloses that gases with moisture levels on the order of two parts per billion can be produced and that such levels can be measured by Atmospheric Pressure Ionization Mass Spectrometry (APIMS). See also T. Kimura, J. Mettes & M. Schack, "Sub-ppb Analysis of Nitrogen Gas by APIMS," presented at the Technical Symposium of SEMICON EAST 89 in Boston, Mass. (September 1989) (disclosing an experimental setup and a procedure for the analysis of high-purity nitrogen).

The present invention focuses on the electrolytic hygrometer. This type of hygrometer operates under the principles of Faraday's Law and incorporates an electrolytic cell as the analytical component. One configuration of an electrolytic cell (a type I cell) consists of a hollow glass tube with two electrodes helically wound around the inside and covered with an hygroscopic film such as phosphorous pentoxide ($P_2O_5$). The two electrodes, one a positive anode and the

2 other a negative cathode, form a double helix. The gas to be measured flows through the cell with a known flow rate.

The water concentration of the gas is determined in the following manner. The hygroscopic film absorbs the water from the gas. A voltage is supplied across the electrodes, which electrolyzes the water in the film into hydrogen and oxygen. The current generated measures the rate at which the water molecules are electrolyzed. Once equilibrium is reached, the rate at which water molecules enter the cell will exactly match the rate at which such molecules are electrolyzed. Consequently, at a given flow rate the water concentration in the gas will be known without any further calibration. An example of a conventional type I electrolytic cell is described in U.S. Pat. No. 4,800,000 to D. Zatko.

A phenomenon called the "recombination effect" can create large errors in the measurement of such electrolytic cells when the sample gas contains substantial amounts of hydrogen or oxygen. The effect refers to the recombination, if a catalyst is present, of hydrogen and oxygen in the cell to re-form water. Thus, a single water molecule can be detected more than once. The catalytic reaction of hydrogen and oxygen will occur on the surface of the precious metal electrodes.

The recombination effect is negligible in inert gases because hydrogen and oxygen produced by electrolysis are present only in very low concentrations. Thus, the probability of molecular collision and reaction of those species is exceedingly small. When the carrier gas contains substantial concentrations of hydrogen or oxygen, however, the probability of reaction increases. In hydrogen gas, for example, oxygen produced by electrolysis can easily collide with surrounding hydrogen and recombine to form water.

The mechanisms for electrolysis and recombination differ. The former is a forced reaction which occurs with energy input at the metal electrodes under the influence of a powerful DC electric field; recombination requires a catalyst and is highly exothermic. Electrolytic hygrometry, the recombination effect, and the factors that affect recombination are described in D. Smith & J. Mitchell, Jr., *Aquametry* (Part II), pages 661–674, 1056 (2d ed. 1984).

In particular, the *Aquametry* reference suggests that, because catalysts and catalyst poisons are familiar associates, very small additions of certain catalyst poisons might render the catalytic surfaces more or less completely and permanently inactive. Exposure of the cell electrodes to $H_2S$, $I_2$ vapor, $CS_2$, HCN, $PH_3$, and $AsH_3$ is proposed to potentially eliminate the recombination problem. The reference indicates that $I_2$ vapor or $H_2S$ might be good candidates for early trial by injection into the sample gas and $HgCl_2$ could be added to the cell as a dilute aqueous solution before the $H_3PO_4$ solution is admitted to coat the electrode wires.

In addition to the recombination effect discussed above, the response time of an hygrometer is an important issue. Conventional hygrometers tend to react slowly to changes, especially when measuring very small concentrations. One of the reasons for perceived slowness, which has nothing to do with the hygrometer, is the "sticky" nature of the water molecule. This characteristic of water makes small changes slow in reality.

With respect to the electrolytic cell itself, one reason for slow response time is the fact that, in order to reflect a change in the moisture concentration of the sample gas, the moisture content of the phosphoric acid film must change. In an equilibrium situation, a certain state of wetness of the film corresponds to a certain film resistivity and, consequently, to a certain resistance for a given configuration. See D. Smith & J. Mitchell, Jr., supra, at pages 535–36. A new equilibrium state will be approached in an exponential way as the difference between the number of incoming and electrolyzed water molecules becomes increasingly small. It is this difference that makes the film move toward the new state. In general, the less film material, the faster the change because the same number of water molecules represents a larger change in the percentage moisture content of the film.

Non-electrolizable areas of the film will slow the response time considerably. These areas exist where there is no, or an insignificant, electric field such as on top of the electrodes, between the glass and the electrodes, in cavities within the glass, and at the ends of the glass tube. As long as these areas contact electrolizable phosphoric acid, moisture will migrate by diffusion, which is a very slow process.

Another issue is the detection limit. Ultimately, even assuming that the sample gas is perfectly dry and that no other sources of moisture molecules capable of absorption by the phosphoric acid film are present (background), the electrolysis current is still not equal to zero. The film moisture content at any moment has some value corresponding to some resistance and, consequently, produces an electrolysis current. If no moisture enters with the gas, this film moisture content will go toward zero at an increasingly slow rate. When further dry-down is measured in days, the achieved level is considered the "stable" background of the cell. The resistance related to this "background" will be lower when there is less film material and with less phosphoric acid in the non-electrolizable areas such as those mentioned above.

An unacceptable time lag of the hygrometer may occur, especially in response to a rise in moisture concentration, after the hygrometer is connected to a very dry gas for a long period. The presence of dry gas for a long time will cause the components of the hygrometer which contact the gas to become dry themselves. Those components include plastic (e.g., polytetrafluoroethylene (PTFE)) tubes and packing materials, like epoxy, which are known to be relatively porous and to absorb or emit moisture from or into a passing gas stream. Such components are described in U.S. Pat. No. 5,198,094 issued to J. Mettes. In addition, part of the moisture coming into a previously dry cell will be absorbed by non-electrolizable phosphoric acid, such as that present on top of the electrodes, and will impact the electrolysis current only after the moisture diffuses toward electrolizable areas.

When an hygrometer encounters a dry gas having a moisture concentration below its detection limit, the instrument will produce a background level reading. In contrast to that reading and in reality, however, the hygrometer and its components will attain an equilibrium corresponding to the lower (undetectable) moisture level. When the moisture concentration subsequently changes to a higher level, certain internal components of the hygrometer will, because they are dry, absorb the moisture before the gas reaches the analyzer. Consequently, it will be some time before the hygrometer senses the increased moisture and can activate an alarm or show the higher concentration.

The amount of time depends, among other things, on how dry the gas was and on how long the dry gas flowed. The process monitored by the hygrometer may be using gas with an unacceptably high moisture concentration for a relatively long time, therefore, before the hygrometer "reads" the correct concentration and activates an alarm. For many applications, such a time lag is unacceptable.

To overcome the problem of recombination in, and to reduce the response time of, a type I electrolytic hygrometer, a new design for and process of manufacturing the detecting unit of the hygrometer is provided. Accordingly, one object of the present invention is to assure minimal recombination errors when an electrolytic hygrometer is used. Another object is to reduce the response time required for an hygrometer to detect and measure an increase in the moisture concentration of the sample gas measured by the hygrometer. A related object is to provide an hygrometer with a low detection limit. It is still another object of the present invention to render the process of manufacturing the detecting unit of the electrolytic hygrometer easier, faster, more reproducible, of higher yield, and less expensive.

SUMMARY OF THE INVENTION

To achieve these and other objects, and in view of its purposes, the present invention provides a new design for and an improved process of manufacturing a detecting unit for a type I electrolytic cell with thin film electrodes. The design for the detecting unit includes a long, narrow, transparent, hollow glass tube. First and second thin, flat, noble metal, film electrodes are deposited on the inside surface of the glass tube and are separated by spacer areas. The two electrodes have the shape of a double helix. The two spacer areas between the electrodes also have the shape of a double helix. An hygroscopic film is deposited on the entire inside surface of the glass tube, covering completely the first and second electrodes and the spacer areas.

In the first step of the process of manufacturing the detecting unit, the long, narrow, transparent, hollow glass tube is provided having an inside surface, an outside surface, and an end with a rim. A thin, noble metal film is deposited on the inside surface of the hollow glass tube. Then, a beam from a light source is directed through the hollow glass tube to remove a first portion of the noble metal film from the inside surface of the hollow glass tube and create the first spacer area. The beam from the light source also removes a second portion of the noble metal film from the inside surface of the hollow glass tube and creates the second spacer area. Consequently, two, separate electrode wires are created. Finally, the hygroscopic film is deposited on the entire inside surface of the hollow glass tube, covering completely the first and second electrode wires and the spacer areas.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing, in which.

DETAILED DESCRIPTION OF THE INVENTION

Figure 1:
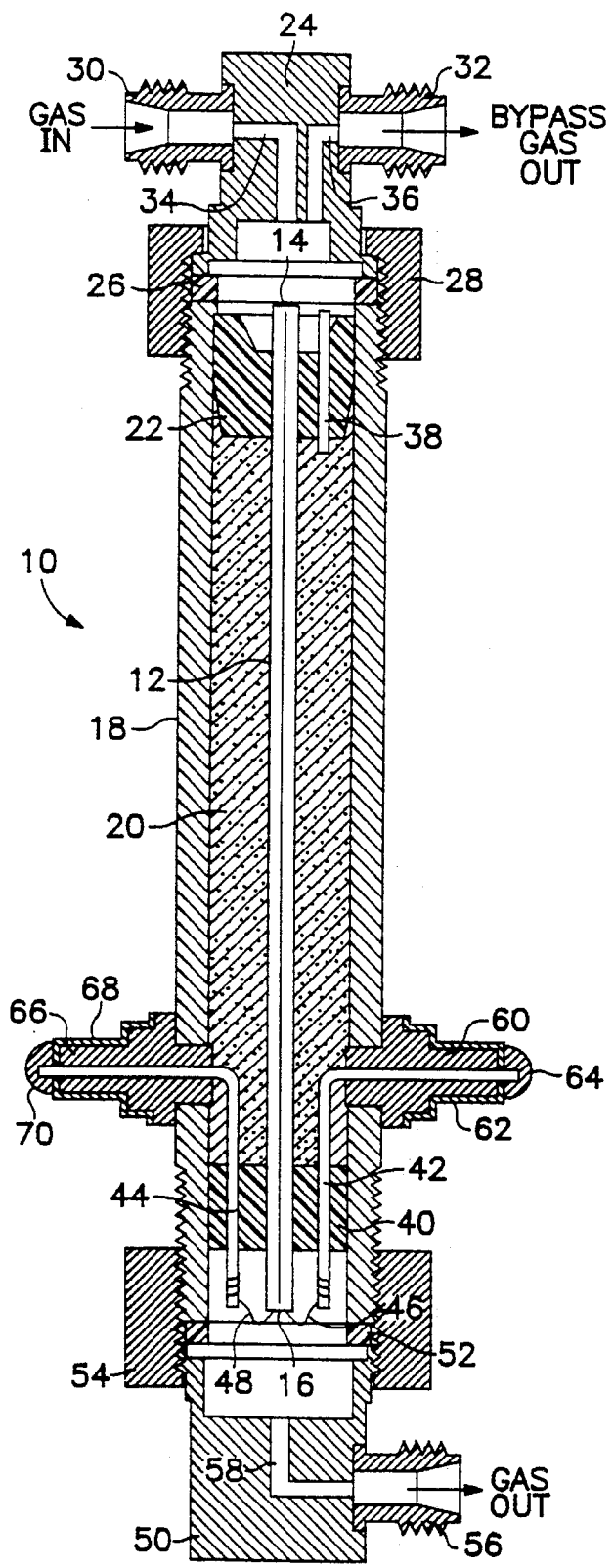
FIG. 1 is a longitudinal, cross-sectional view of a conventional type I electrolytic cell as disclosed in U.S. Pat. No. 4,800,000 to D. Zatko.

Referring now to the drawing, like reference numerals refer to like elements throughout. It is emphasized that, according to common practice in semiconductor representation, the various components of the drawing are not to scale. On the contrary, the width or length or thickness of the various components are arbitrarily expanded or reduced for clarity.

Referring specifically to FIG. 1, an electrolytic cell 10 is known which includes a tubular glass detecting unit 12. Detecting unit 12 passes a gas and has an inlet 14 and an outlet 16. Unit 12 is positioned concentrically in a stainless steel protective housing 18. A packing material 20, typically an epoxy potting compound, fills the concentric area between unit 12 and housing 18.

An inlet plug 22 surrounds and concentrically positions unit 12 at the inlet end of cell 10. An inlet cap 24 is mounted in sealing engagement with a gasket 26 on the upper end of housing 18, and is fixed in position by a nut 28. Fittings 30, 32 are mounted as arms transversely of cap 24 and attach gas inlet and bypass gas outlet lines, respectively (not shown). Channel 34 conveys gas from fitting 30 through cap 24 to inlet 14 of unit 12. Channel 36 is a bypass conduit connecting cap 24 to fitting 32 to pass gas from a source connected to fitting 30 to a collector connected to fitting 32.

Extending through plug 22 is a tube 38 to admit epoxy 20 during manufacture of cell 10. Tube 38 is plugged upon setting by epoxy 20.

The outlet end of unit 12 is concentrically positioned in housing 18 by plug 40. Electrode leads 42, 44, positioned in plug 40, are connected to the free ends of wires 46, 48 helically covering the interior of unit 12. Wires 46, 48 are usually made of platinum, iridium, rhodium, or another noble metal. Gold may also be suitable. A bottom cap 50 seats on a gasket 52 and is sealed to and mounted on housing 18 by a nut 54. A gas outlet fitting 56 is mounted in cap 50 as a side arm and receives gas from the interior of cap 50 and unit 12 via a channel 58. Lead 42 extends externally of housing 18 through an electrically insulating packing 60 within a metallic contact arm 62 having a soldered tip 64. Similarly, lead 44 is received in an electrically insulating packing 66 in a metallic contact arm 68 mounted in housing 18 and having a soldered tip 70.

Wires 46, 48 are helically wound substantially the full length of unit 12 and are exposed to gas passing from inlet 14 to outlet 16. The interior of unit 12, including wires 46, 48, is coated with a water absorbent (hygroscopic) film (such as phosphorous pentoxide, not shown) which will conduct the ions resulting from electrolysis of the moisture between the two electrodes. The electrolysis current will match the rate at which moisture molecules enter unit 12 when the system is in equilibrium. Detecting unit 12 is very long and narrow (on the order of 1 mm inside diameter and 100 mm length) to ensure that substantially all of the moisture in the gas contacts the hygroscopic film. Consequently, all water in the gas passing through detecting unit 12 will be subjected to electrolysis.

In moisture analysis by electrolytic hygrometry, water reacts with the hygroscopic film in contact with wires 46, 48 in electrolytic cell 10. The water in the film is electrolyzed by an applied voltage to produce hydrogen and oxygen. The resulting current is an absolute measure of the rate of water absorption by the cell under Faraday's Law.

Erroneously high water readings for electrolytic hygrometers are caused by the recombination of hydrogen and oxygen to re-form water when the sample gas contains substantial amounts of hydrogen or oxygen. The recombination reaction proceeds according to the formula:

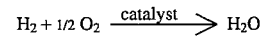

$$H_2 + 1/2\, O_2 \xrightarrow{\text{catalyst}} H_2O$$

Both the noble metals and their oxides catalyze the recombination reaction. In fact, a main source of recombination is the catalytic activity of electrode wires 46, 48 in electrolytic cell 10.

Minimization of recombination errors is important when an electrolytic hygrometer is used for industrial applications. It is important, for example, in the semiconductor industry where monitoring and controlling moisture in hydrogen- or oxygen-containing atmospheres affects product yield and quality.

Figure 2:
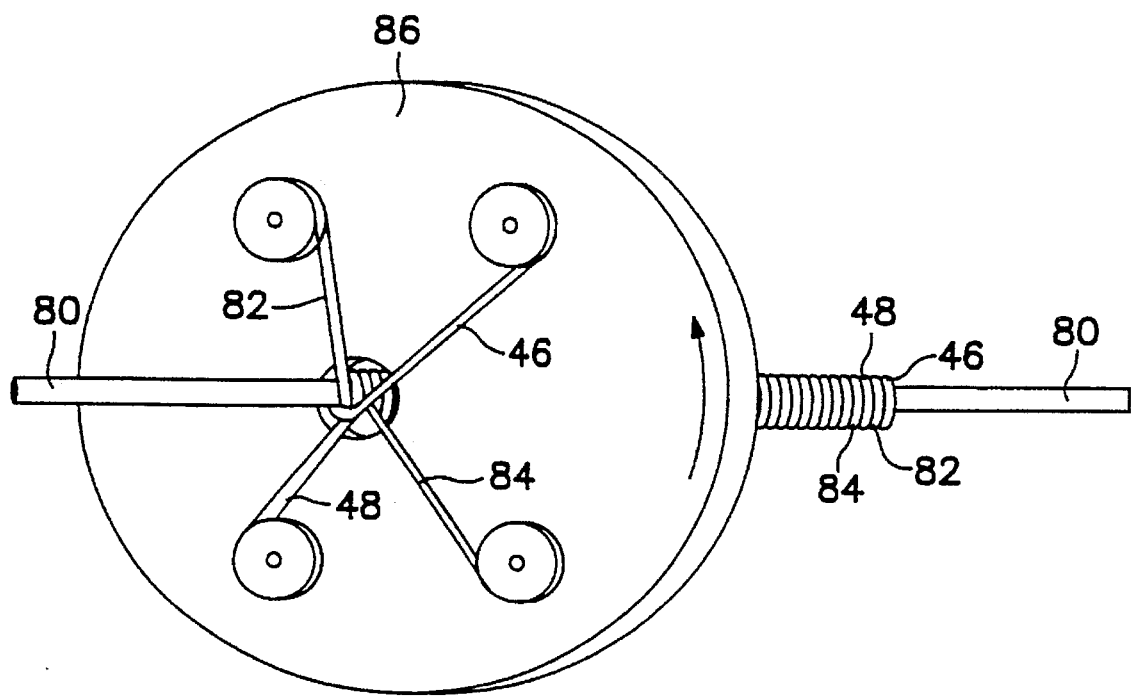
FIG. 2 illustrates the mandrel and the rotating winder used in the conventional process to fabricate the detecting unit of the type I electrolytic cell shown in FIG. 1.

The traditional way to fabricate detecting unit 12 of type I electrolytic cell 10 begins with a stainless steel mandrel 80 (see FIG. 2). Two, thin, platinum wires 46, 48, alternating with two, thin copper wires 82, 84, are wound tightly around mandrel 80 using a rotating winder 86. Copper wires 82, 84 hold wires 46, 48 in place on mandrel 80. Wires 46, 48 and copper wires 82, 84 may each have a diameter of about 0.125 mm. The ends of the wires 46, 48, 82, 84 are soldered at a predetermined length corresponding to the length of detecting unit 12 desired. Then, mandrel 80, with wires 46, 48, 82, 84 wound around it, is removed from winder 86.

Figure 3:
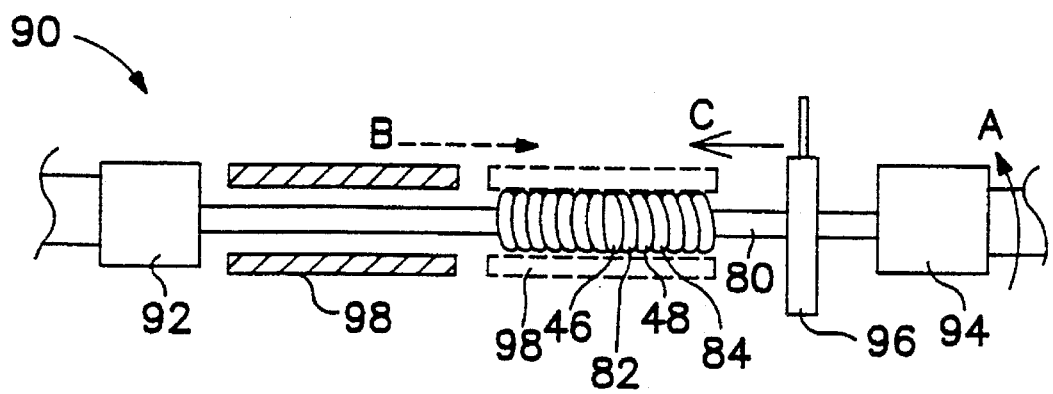
FIG. 3 illustrates the sealing device used in the conventional process to fabricate the detecting unit of the type I electrolytic cell shown in FIG. 1.

Wound mandrel 80 is placed in the sealing device 90 shown in FIG. 3. Sealing device 90 may be rotated as shown by arrow A. Opposite ends of mandrel 80 are held by opposing chucks 92, 94. A heating coil 96 surrounds mandrel 80. Also surrounding mandrel 80 is the glass tube 98 which will be used to form detecting unit 12. Three, separate steps are performed, during the manufacture of detecting unit 12, in sealing device 90.

First, the step of degassing is performed. This step removes impurities. A crust of copper oxide often forms, however, during this degassing step. Undesirable effects of the formation of this copper oxide crust are discussed below. Attempts to prevent copper oxide formation, such as degassing in an inert (e.g., hydrogen) atmosphere, have proven unsuccessful.

The second step performed in sealing device 90 is to shift (in the direction of the dotted, arrow B) glass tube 98 over wires 46, 48, 82, 84 on mandrel 80. Glass tube 98 assumes the position shown by the dotted lines in FIG. 3. This step occasionally dislodges flakes of copper oxide formed during the degassing step; such flakes rest on the surface of wires 46, 48, 82, 84.

Finally, wires 46, 48, 82, 84 are sealed in glass tube 98. This sealing step involves passing heating coil 96 over glass tube 98 in the direction of arrow C. The temperature of heating coil 96 is sufficient to melt glass tube 98 so that glass flows down approximately half the diameter of wires 46, 48, 82, 84 before the glass resolidifies or hardens. Consequently, electrode wires 46, 48 will extend inside the diameter of gas detecting unit 12 by about half their diameter, thereby providing adequate area for contact with the gas stream under test.

Once wires 46, 48, 82, 84 are sealed in glass tube 98, mandrel 80 is placed in a pulling device (not shown). Opposite ends of the mandrel are grasped and pulled by the device. Mandrel 80 is stretched and, therefore, becomes thinner. This allows mandrel 80 to slide out from wires 46, 48, 82, 84 and glass tube 98, leaving glass tube 98 with wires 46, 48, 82, 84 sealed therein.

Copper wires 82, 84, having performed their function, are then dissolved in strong nitric acid ($HNO_3$). Glass tube 98 is installed in housing Finally, the hygroscopic film (typically phosphorous pentoxide, $P_2O_5$) is deposited on the inner diameter of glass tube 98 and over electrode wires 46, 48. All of these steps are well known in the art.

Thus, the conventional fabrication of detecting unit 12 of type I electrolytic hygrometer 10 requires a delicate process wherein glass tube 98 is melted in a manner designed to half cover the thin electrode wire coil when it hardens. This step is not only difficult to reproduce, it poses numerous quality problems. As examples, bubbles in the glass and poor (electrode) metal-to-glass contact cause rejects and reduce manufacturing yield.

The conventional process for manufacturing the detecting unit 12 of type I electrolytic hygrometer 10, as outlined above, nevertheless results in a useful hygrometer. The performance characteristics of such an hygrometer can be improved, however, by addressing several drawbacks found in the hygrometer. These drawbacks are attributable to at least three features of the conventional manufacturing process.

The hygrometer manufactured in accordance with the conventional process has a relatively large amount of "dead" mass of non-electrolyzable hygroscopic film. Although an electric field is necessary to electrolyze water molecules, no field will be present on top of a metal surface because the electric potential is constant on a metal surface. This will be the case for the film on the electrodes, for the portion of the electrodes not embedded in the glass, but could be true even for the film found between the glass and the electrodes when poor bonding exists. Non-electrolyzable hygroscopic film slows the response of the hygrometer to changes in the moisture content of the gas stream under measurement. Pockets of non-electrolyzable hygroscopic film also cause a high background signal.

Such pockets are formed during the sealing step of the conventional manufacturing process. The material properties (e.g., thermal expansion) of the glass used to make glass tube 98 and the metal used to make wires 46, 48 must be matched carefully. Typically, a relatively "soft" glass and platinum or rhodium metal are selected. Even with careful matching, however, the adherence between the glass and metal is imperfect upon cooling and solidification of the glass. Consequently, spaces or pockets form between the glass and metal. The hygroscopic film enters these areas as it is deposited on the inner diameter of glass tube 98.

Second, as noted above, a crust of copper oxide often forms during the conventional degassing step. Upon shift of glass tube 98 over wires 46, 48, 82, 84 on mandrel 80, flakes of copper oxide are dislodged and rest on the surface of wires 46, 48, 82, 84. These flakes become embedded in the glass upon melting and resolidification. Subsequently, upon etching, cavities are formed in the glass where the flakes had become embedded. Such cavities also store hygroscopic film material from which moisture is removed by diffusion rather than electrolysis. There is a relatively small area of gas contact for the volume of film involved in such cavities.

Finally, trapped air, vaporized contaminants, or both form bubbles in the glass during the conventional sealing step. These bubbles can store non-electrolyzable hygroscopic film as it is deposited on the inner diameter of glass tube 98. The non-electrolyzable hygroscopic film is especially problematic when it contacts the electrode coil (i.e., wires 46, 48). This occurs when the bubbles (or cavities, spaces, or pockets) are formed adjacent the electrode coil.

The conventional sealing step also enhances recombination indirectly. Although the noble metals used to form the electrodes (e.g., platinum, rhodium, iridium, and the like) catalyze the recombination reaction only minimally, having a negligible effect on hygrometer sensitivity, the noble metal oxides are active catalysts. See D. Smith & J. Mitchell, Jr., supra, at 663. Once formed, the oxides of the noble metals retain their oxygen with tenacity. Oxidation of the electrode wires occurs during the sealing step and, therefore, the sealing step indirectly promotes recombination.

In addition, large surface areas favor catalytic activity and, consequently, the recombination reaction. See D. Smith & J. Mitchell, Jr., supra, at 663. The round electrode wires used in the conventional manufacturing process provide a large surface area. Hydrogen ($H_2$) and oxygen ($O_2$) can reach the noble metal electrode, which acts as the catalyst in the recombination reaction. The phosphorous pentoxide film covering the electrodes reduces the recombination problem because the hydrogen and oxygen gases must pass through the film. Of course, large electrode surface areas not covered by phosphorous pentoxide exacerbate the recombination problem.

Figure 4:
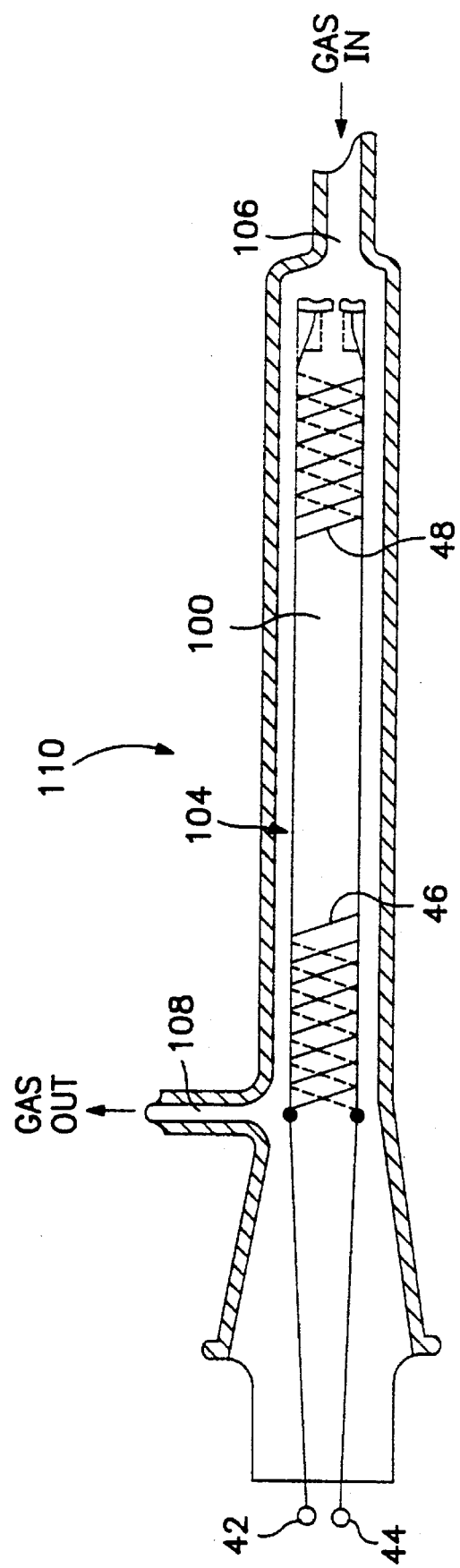
FIG. 4 is a longitudinal, cross-sectional view of a conventional type II electrolytic cell as disclosed in D. Smith & J. Mitchell, Jr., supra, at page 530.

The literature suggests theoretical, unrealistic configurations for a type II electrolytic cell that minimize recombination. See D. Smith & J. Mitchell, Jr., supra, at 673–74. The detecting unit 110 for a basic type II electrolytic cell is illustrated in FIG. 4 (with the housing). An inner, solid (or at least closed) glass cylinder 100 is provided. Helical grooves are machined (milled) in the outside surface of glass cylinder 100. The electrode wires 46, 48 are placed in the grooves so that electrode wires 46, 48 are about 20% encapsulated. Electrode leads 42, 44 connect electrode wires 46, 48 to external equipment.

Concentric with inner cylinder 100 is an outer sleeve 102. Typically, outer sleeve 102 is made of PTFE. A small clearance 104 (about 0.5 mm) is provided between inner cylinder 100 and outer sleeve 102. In operation, the sample gas having moisture to be measured enters the inlet 106 of outer sleeve 102 and passes around inner cylinder 100 in clearance 104. The gas does not enter inner cylinder 100. Consequently, the moisture in the gas contacts the phosphorous pentoxide film on wires 46, 8 and its content is measured. The gas then exits through outlet 108 of outer sleeve 102.

The basic type II electrolytic cell design of detecting unit 110 shown in FIG. 4 can be modified somewhat in order to minimize recombination. Wires 46, 48 can be set flush with the surface of inner cylinder 100. This protects detecting unit 110 against agglomeration or viscous flow of the phosphorous pentoxide film under all but the most prolonged, severe, service operating conditions. Consequently, wires 46, 48 remain covered with a continuous film of phosphorous pentoxide—which reduces recombination.

The success of an electrolytic cell depends primarily on its ability to assure that most or all of the moisture in the gas being sampled is placed in intimate contact with the phosphorous pentoxide film. The glass tube 98 of the detecting unit 12 in type I electrolytic cells 10 can be made very long and narrow (i.e., small diameter), and the inside surface of glass tube 98 can be completely covered with the phosphorous pentoxide film, thereby assuring that almost all moisture contacts the phosphorous pentoxide film. In contrast, the detecting unit 110 of the type II electrolytic cell offers an inferior sample gas-to-phosphorous pentoxide film contact.

Another advantage of the type I over the type II electrolytic cell is that part of the non-electrolyzable film material can more easily be removed from a type I detecting unit. The interior of the glass tube is covered by electrodes and phosphoric acid film. Any film that exists beyond the area of the electrodes will automatically be located toward the outside ends of the glass element and will create a problem only when that film remains in contact with the electrolyzable film located on the electrodes. Such contact will occur by diffusion which is a very slow process. Fortunately, the outside ends of the glass element of a type I cell can be rigorously cleaned without damaging the film located on the electrodes. In contrast, a type II cell poses more of a problem because the body that supports the electrode wires extends beyond the area where the electrodes are located. Advantages such as those described above have enabled the type I electrolytic cell to reach extremely low detection limits with relatively fast response times. Consequently, the dominating hygrometers found in ultra high purity applications such as semiconductor manufacturing are the type I electrolytic cells.

The extremely long and narrow geometry of glass tube 98 used in detecting unit 12 creates problems, however, during the manufacturing process. Specifically, it is difficult to work with and on other components (e.g., wires 46, 48 and the phosphorous pentoxide film) of detecting unit 12 which are disposed inside glass tube 98. These components are relatively inaccessible.

Figure 5:
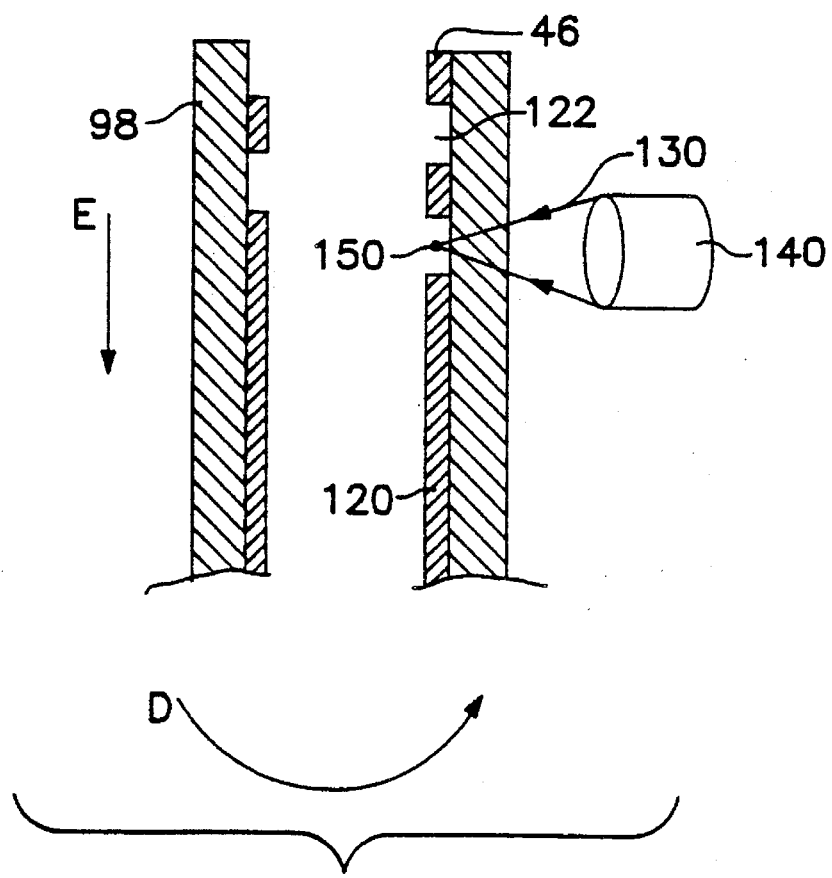
FIG. 5 illustrates a first embodiment of the improved process, according to the present invention, for manufacturing the detecting unit of a type I electrolytic cell with thin film electrodes.

A first embodiment of the improved process for manufacturing the detecting unit 12 of a type I electrolytic cell 10 with thin film electrodes is illustrated in FIG. 5. A thin, noble metal film 120 is deposited on the inside of glass tube 98. Deposition can be done by evaporation, sputtering, or other known deposition techniques. Platinum is preferred because its coefficient of expansion is close to that of many types of glass. Although the thickness of noble metal film 120 may vary, depending upon the application, it is typically between 0.03 and 0.06 mm.

One procedure for applying a tenacious film of platinum to Pyrex® glass is described by D. Smith & J. Mitchell, Jr., supra, at 1151, 1152, and 1128. A mixture is prepared of 0.2 g chlorplatinic acid (or platinic chloride), 5 ml each of alcohol and ethyl ether, plus 4 or 5 drops of turpentine. This mixture is applied carefully to the scrupulously cleaned inner surface of hollow glass tube 98. The mixture can be poured through glass tube 98 for this purpose. Glass tube 98 is heated, staying largely below its melting point, to remove adhering liquid. The result is a film 120 of platinum metal covering the inside surface of glass tube 98.

A strong, focused laser beam 130 is directed by laser beam source 140 through transparent glass tube 98. Laser beam 130 is sufficiently well-focused to form a small spot 150—an area of highly localized heating—on noble metal film 120. Laser beam 130 removes part of film 120 by vaporizing or evaporating the noble metal or the glass that supports it. Laser beam 130 can be re-directed, or a second beam can be directed simultaneously, to provide a double helix ribbon formed by positive anode and negative cathode electrode wires 46, 48 separated by spacer areas 122. During the evaporation step, a fluid (gas or liquid) is passed through glass tube 98. This flow removes noble metal fragments, provides cooling, or both. Because laser beam 130 goes through glass tube 98, the process circumvents the inaccessibility problem encountered with prior art manufacturing processes.

Various parameters of laser beam 130 must be controlled, of course, to assure the desired formation of wires 46, 48. Such parameters include the wavelength, beam diameter, beam divergence, and the like. The index of refraction of the glass and geometry of the glass used to make glass tube 98 also must be taken into account. Finally, glass tube 98 (or, alternatively, laser source 140) must be rotated and translated to obtain the desired, double helix shaped pattern for wires 46, 48. Rotation may be in the direction of arrow "D," and translation in the direction of arrow "E," in FIG. 5. Computer software facilitates maximization of these design parameters.

The tendency of the noble metal forming film 120 to reflect the light of laser beam 130 might be overcome by mixing a light-absorbing component into the noble metal used to make wires 46, 48.

Because they provide less surface area than round electrode wires, flat electrode wires 46, 48 help to solve the recombination problem that plagues hygrometers. Extremely narrow, thin electrode wires 46, 48 also avoid a large, noble metal surface area. The process of the present invention can precisely control the geometry of wires 46, 48.

Figure 6A:
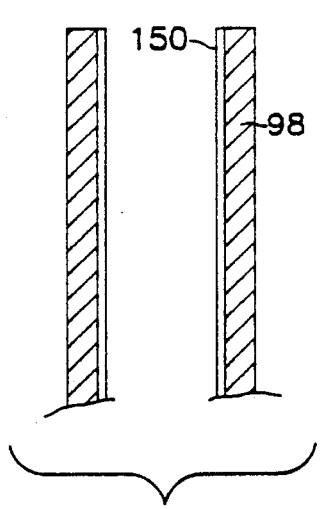
FIGS. 6a, 6b, 6c, and 6d illustrate four steps in a second embodiment of the improved process, according to the present invention, for manufacturing the detecting unit of a type I electrolytic cell with thin film electrodes.

An alternative embodiment of the present invention is illustrated in FIGS. 6a, 6b, 6c, and 6d. An intermediate layer 150, which can be removed more easily than the noble metal film 120, is deposited on the inside surface of glass tube 98. This step of the process is shown in FIG. 6a. Intermediate layer 150 is, for example, a photoresist.

Intermediate layer 150 is then removed (in a double helix pattern) from those areas of glass tube 98 where noble metal wires 46, 48 will be located. A photoresist intermediate layer can be removed by activating the photoresist with ultraviolet light 160 from a light source 170. As discussed above, glass tube 98 (or, alternatively, light source 170) must be rotated and translated to obtain the desired, double helix shaped pattern for wires 46, 48. Rotation may be in the direction of arrow "F," and translation in the direction of arrow "G," in FIG. 6b. Computer software may again be used to control the process parameters.

Figure 6C:
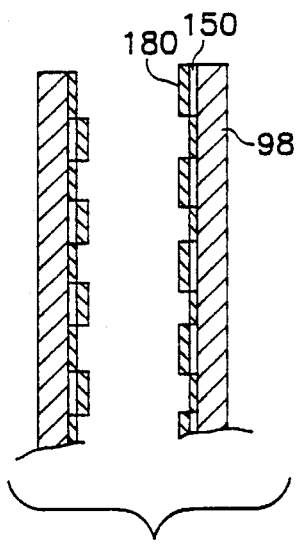
Figure 6B:
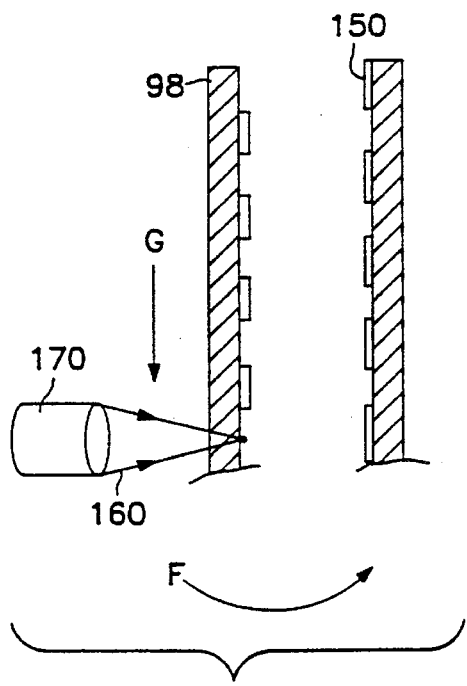
Figure 6D:
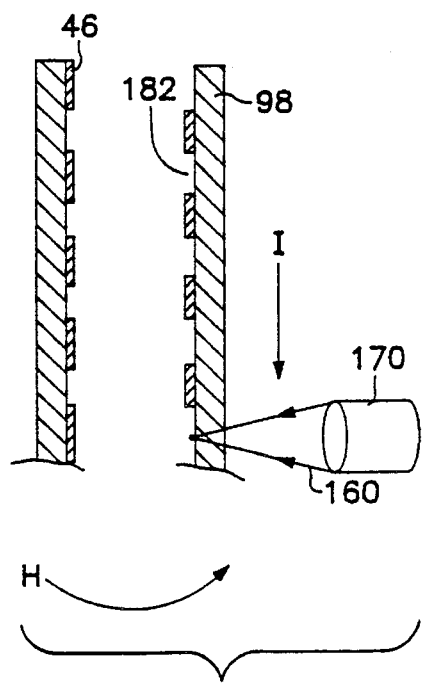

Then, the noble metal film 180 is deposited (see FIG. 6c). Finally, the remaining intermediate layer 150, with noble metal film 180 on top, is removed—leaving wires 46, 48 and spacer areas 182 without noble metal between wires 46, 48. Removal is accomplished by activating the photoresist with ultraviolet light 160 from light source 170. Rotation of glass tube 98 (or, alternatively, light source 170) may be in the direction of arrow "H," and translation in the direction of arrow "I," in FIG. 6d. Computer software may once again be used to control the process parameters.

Figure 7:
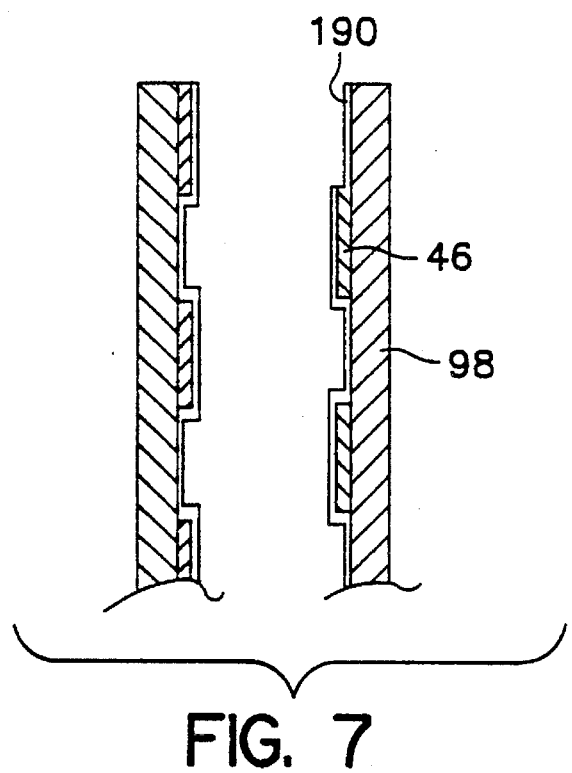
FIG. 7 illustrates the detecting unit manufactured in accordance with the present invention.

Regardless of which alternative embodiment of the process described above is used to form wires 46, 48, a phosphorous pentoxide film 190 is deposited over the entire inside surface of glass tube 98. Thus, phosphorous pentoxide film 190 completely covers both wires 46, 48 and spacer areas 122 or 182. The resulting detecting unit 12 is shown in FIG. 7.

Wires 46, 48 must be connected to external equipment. In conventional type I electrolytic cells (see FIG. 1), this connection is accomplished via electrode leads 42, 44. Electrode leads 42, 44 are typically soldered to wires 46, 48. It is difficult to solder electrode leads 42, 44 to wires 46, 48 inside glass tube 98 because wires 46, 48 are relatively inaccessible. Moreover, the soldering process itself creates undesirable risks, contamination, or both.

Figure 8:
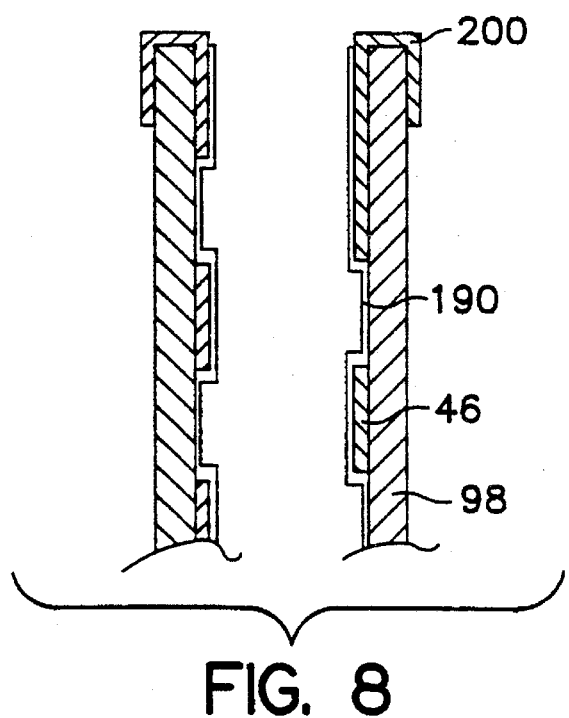
FIG. 8 shows the noble metal coating deposited by the process of the present invention over the rim of, and partially down the outside of, the glass tube of the detecting unit.

As shown in FIG. 8, the present invention provides a noble metal coating 200 around the ends of glass tube 98 (over the rim of glass tube 98) and partially down the outside of glass tube 98. Electrode leads 42, 44 can then be soldered to coating 200 outside glass tube 98. Even more advantageously, glass tube 98 can be press-fit into physical and electrical contact with external equipment. This avoids any need to solder components. Thus, coating 200 permits electrical contact between wires 46, 48 and external equipment. The type I electrolytic cell 12 manufactured in accordance with the improved process of the present invention can be installed in housing 18 of new cells or used to retrofit existing cells.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed is:

1. A process of manufacturing a detecting unit for an electrolytic cell with thin film electrodes comprising the steps of:
    (a) providing a long, narrow transparent, hollow glass tube having an inside surface, an outside surface, and an end with a rim;
    (b) depositing a thin, noble metal film on the inside surface of the hollow glass tube;
    (c) directing a beam from a light source through the hollow glass tube to remove first and second portions of the noble metal film from the inside surface of the hollow glass tube and create first and second thin film electrodes separated by spacer areas; and
    (d) depositing an hygroscopic film on the entire inside surface of the hollow glass tube, covering completely the first and second electrodes and the spacer areas.

2. The process according to claim 1 wherein the hygroscopic film is phosphorous pentoxide.

3. The process according to claim 1 wherein the noble metal film is platinum.

4. The process according to claim 1 further including, simultaneously with the step (c) of directing the beam, the step of passing a fluid through the hollow glass tube.

5. The process according to claim 1 wherein the step (c) of directing the beam includes rotating and translating the light source relative to the hollow glass tube.

6. The process according to claim 1 further comprising the step (e) of depositing a noble metal coating around the end and over the rim of the hollow glass tube.

7. The process according to claim 1 wherein the light source is a laser.

8. The process according to claim 1 further comprising, before the step (b) of depositing the noble metal film on the inside surface of the hollow glass tube, depositing an intermediate layer on the inside surface of the hollow glass tube and removing portions of the intermediate layer from those sections of the hollow glass tube where the first and second thin film electrodes will be formed.

9. The process according to claim 8 wherein the intermediate layer is a photoresist and the light source emits ultraviolet light.

10. the process according to claim 1 wherein the noble metal film is deposited on the inside surface of the hollow glass tube by one of evaporation and sputtering.

11. A process of manufacturing a detecting unit for an electrolytic cell with thin film electrodes comprising the steps of:
    (a) providing a long, narrow, transparent, hollow glass tube having an inside surface, an outside surface, and an end with a rim;
    (b) depositing a thin, noble metal film directly on the inside surface of the hollow glass tube;
    (c) directing a laser beam from a laser source through the hollow glass tube and onto first and second portions of the noble metal film to remove the first and second portions of the noble m etal film from the inside surface of the hollow glass tube and create first and secon thin film electrodes separated by spacer areas; and
    (d) depositing an hygroscopic film on the entire inside surface of the hollow glass tube, covering completely the first and second electrodes and the spacer areas.

12. The process according to claim 11 further comprising, before the step (b) of depositing the noble metal film, the step of mixing a light-absorbing component into the noble metal.

13. The process according to claim 11 further including, simultaneously with the step (c) of directing the beam, the step of passing a fluid through the hollow glass tube.

14. The process according to claim 11 wherein the step (c) of directing the beam includes rotating and translating the laser source relative to the hollow glass tube.

15. The process according to claim 11 further comprising the step (e) of depositing a noble metal coating around the end and over the rim of the hollow glass tube.

16. A process of manufacturing a detecting unit for an electrolytic cell with thin film electrodes comprising the steps of:
    (a) providing a long, narrow, transparent, hollow glass tube having an inside surface, an outside surface, and an end with a rim;
    (b) depositing an intermediate layer directly on the inside surface of the hollow glass tube;
    (c) directing a beam from a light source through the hollow glass tube and onto a first segment of the intermediate layer to remove the first segment of the intermediate layer from the inside surface of the hollow glass tube while leaving a remaining segment of the intermediate layer on the inside surface of the hollow glass tube;
    (d) depositing a thin, noble metal film on the inside surface of the hollow glass tube and over the remaining segment of the intermediate layer;
    (e) re-directing the beam from the light source through the hollow glass tube and onto the remaining segment of the intermediate layer to remove the remaining segment of the intermediate layer and the noble metal film over the remaining segment of the intermediate layer, creating a first thin film electrode and a second thin film electrode separated from the first electrode by spacer areas; and (f) depositing an hygroscopic film on the entire inside surface of the hollow glass tube, covering completely the first and second electrodes and the spacer areas.

17. The process according to claim 16 further including, simultaneously with the steps (c) of directing the beam and (e) of re-directing the beam, the step of passing a fluid through the hollow glass tube.

18. The process according to claim 16 wherein the steps (c) of directing the beam and (e) of re-directing the beam include rotating and translating the light source relative to the hollow glass tube.

19. The process according to claim 16 further comprising the step (g) of depositing a noble metal coating around the end and over the rim of the hollow glass tube.

20. The process according to claim 16 wherein the intermediate layer is a photoresist and the light source emits ultraviolet light.

21. The process according to claim 16 wherein the hygroscopic film is phosphorous pentoxide.

22. The process according to claim 16 wherein the noble metal film is platinum.

* * * * *